United States Patent [19]

Srinivasan et al.

[11] 4,062,727

[45] Dec. 13, 1977

[54] PROCESS FOR MANUFACTURING HIGH DENSITY CELL CULTURES

[75] Inventors: Vadake R. Srinivasan, Baton Rouge, La.; Marvin B. Fleenor, St. Louis, Mo.; Richard J. Summers; Margaret W. Bumm, both of Baton Rouge, La.

[73] Assignee: Louisiana State University Foundation, Baton Rouge, La.

[21] Appl. No.: 674,855

[22] Filed: Apr. 8, 1976

[51] Int. Cl.$^2$ .............................................. C12B 1/00
[52] U.S. Cl. .................................. 195/28 R; 195/33; 195/82; 195/96; 195/117
[58] Field of Search .............. 195/28 R, 96, 104, 108, 195/115, 118, 117, 82

[56] References Cited

U.S. PATENT DOCUMENTS

| | | | |
|---|---|---|---|
| 2,822,319 | 2/1958 | Monod | 195/115 |
| 3,342,695 | 9/1967 | Felsenfeld | 195/115 |
| 3,761,355 | 9/1973 | Callihan et al. | 195/33 |

*Primary Examiner*—R. B. Penland
*Attorney, Agent, or Firm*—Llewellyn A. Proctor

[57] ABSTRACT

A process for biosynthetically producing cells in a liquid fermentation media comprised of a carbon source, and a growth medium containing oxygen and other essential cell nutrients, to obtain a biomass for harvesting. The carbon source and each of the other essential cell nutrients are added, incrementally or continuously, to the fermentation media, and each required nutrient is maintained at essentially the minimum level needed for efficient assimilation by the growing cells, in accordance with a predetermined cell growth curve based on the metabolic or respiratory function of the cells which convert the carbon source to a biomass. The process constitutes a marked improvement in accelerating and increasing cell production in a given fermentation system. In its preferred aspects, the nutrients are added within the fermentation media below the foram level which forms on top of the fermentation broth. A particularly preferred fermentation system embodies the preparation, in a nutrient medium, of comestible, digestible protein from a carbon source, suitably a hydrocarbon or carbohydrate, particularly delignified cellulose. A cellulase-elaborating microorganism, suitably a fungii, yeast or bacteria, particularly a microorganism of the genus Cellulomonas (ATCC-21399) used alone, or in compatible association with another microorganism, is cultivated within the medium which contains the carbon source.

6 Claims, No Drawings

PROCESS FOR MANUFACTURING HIGH DENSITY CELL CULTURES

Fermentation processes, as a means for producing useful products or for the elimination of waste, have been under intensive appraisal for the last several years. This is due largely to increasing world populations, thus contributing to the erosion of world resources, particularly food supplies, and the ever increasing pollution problem which is more closely associated with a growing and more affluent society. Maximum production of useful products, and the maximum efficient elimination of wastes is essential.

Fermentation processes have many uses, and such uses are expanding. They are useful in the production of drugs, e.g. antibiotics, hormones, and the like, chemicals, enzymes, starter cultures and food. Various means have been employed to maximize production in fermentation processes, inclusive of processes wherein the carbon or energy source has been supplied to the fermentation media in optimized minimum concentrations to achieve higher production levels.

Exemplary of fermentation processes generally are those which have been found useful for the production of food, notably nutritive protein. Processes for use in the production of comestible, digestible protein by harvesting microorganisms as single cell protein for direct use as food, or food supplements, are of particular importance, and these are now the subject of intensive studies being conducted throughout the world. Because of increasing world populations and a decreasing ability of such populations to feed themselves, efforts in single-cell protein are directed toward the production of animal-type proteins, complex polymers constituted of all or a predominance of some twenty-two amino acids which are essential constituents in the diet of human beings and animals. A variety of microorganisms have been cultivated, and harvested as microbial protein food, or feed supplements, e.g. algae, yeasts and bacteria. Additionally, a wide variety of substrates have been proposed and used as assimilable carbon source nutrients for microbiological fermentation, notably hydrocarbons and carbohydrates.

Whereas hydrocarbons has received much attention as assimilable carbon sources for the production of single-cell protein, limited solubility of the substrate in the growth medium has required somewhat sophisticated technology to overcome this disadvantage. Moreover, long term studies are required to demonstrate the lack of carcinogenesis in hydrocarbon-derived micro-organisms. Much attention has thus now been shifted toward the use of cellulose as a carbon or energy substrate.

Most organisms, albeit they are unable to directly utilize cellulose, are able to metabolize delignified cellulose, and partial hydrolysis of the cellulose as by treatment with alkalis and the like has not been found burdensome. In such treatment the cellulose is degraded, delignified, and rendered susceptible for breakdown by the microorganisms, metabolized, and converted to single-cell protein rich in amino acids. The fungi have been the subject of intensive studies as suitable microorganisms for cultivation because of their ease of production and high cellulase activity. As a source of single-cell protein, however, the yeasts and bacteria have proven particularly desirable because of their higher growth rate, high protein and low cell wall content. Yeasts and bacteria therefore have been extensively cultivated with cellulose in recent years as a source of single-cell protein from cellulose.

In U.S. Pat. No. 3,761,355, e.g. herewith incorporated by reference, there is disclosed a process for converting cellulose to protein by means of microorganisms. Cellulase-elaborating bacteria of the genus Cellulomonas (ATCC 21399) are cultivated on a delignified cellulose substrate, the harvested bacterial cells constituting comestible, digestible protein of high amino acid content. Symbiotic fermentation processes are also known, as e.g. that used for obtaining improved yields of nutritive protein wherein cellulase-producing organism Cellulomonas is grown on delignified cellulose in conjunction with several species of yeasts which utilize the cellobiose, a breakdown product of cellulose.

In a typical process, a cellulose substrate (especially a waste cellulosic material) is ground in an initial step to sufficiently small size to form a "pumpable" slurry, which is alkali treated at a temperature and time sufficient to decrystallize and delignify the cellulose. The alkali-cellulose, after washing, is fed with all of the desired nutrients into a fermentor and the fermentation medium is inoculated with the microorganism to be harvested, suitably Cellulomonas, or possibly a simbiotic admixture of such microorganisms, suitably Cellulomonas and Candida guilliermondii or Trichosporon cutaneum. During fermentation, the temperature is maintained, e.g. at 25°–40° C, and the medium is aerated with air (oxygen) while the pH is maintained at e.g. between about 5 and 9. The medium is continuously agitated during the entire period of fermentation, at the end of which period fermentation ceases and the maximum production of the biomass is achieved. The biomass is then withdrawn from the fermentor as a slurry, flocculant is added to coalesce the cells and the slurry is filtered. Single-cell protein is recovered from the effluent.

Albeit much has been learned, and various microorganisms, notably fungi, yeasts and bacteria, have been successfully, reproducibly cultivated on various types of carbon or energy substrate, notably cellulose, much yet should be done to provide greater yields of a biomass, lessen production periods, utilize more fully the nutrients fed into a process, and in general to lessen capital and production costs.

It is accordingly, the primary objective of the present invention to provide a new and novel process which will achieve notable improvements in cell yields, shorten production periods, more effectively utilize the nutrients in cell production, and in general lower capital requirements and production costs in processes used for the production of biomasses, particularly comestible, digestible protein wherein microorganisms, especially fungi, yeasts and bacteria, are cultivated on a carbon or energy source, notably a hydrocarbon or carbohydrate, and then harvested as a source of protein, enzymes or any other primary metabolite.

A specific object is to provide a process, particularly effective for the conversion of cellulose to nutritive protein in a submerged aerobic culture by the use of yeasts and bacteria, alone or in compatible association.

A more specific object is to provide a process for the conversion of cellulose to nutritive protein by the use of a cellulase-elaborating microorganism, notably a microorganism of the genus Cellulomonas (ATCC-21399), alone or in compatible association with other bacteria, fungi, or yeasts, at conditions which will greatly accelerate the rate of reaction and increase the total biomass produced in a given nutrient medium.

These objects and others are achieved in accordance with the present invention, which comprises a process for biosynthetically producing cells in a liquid fermentation media comprised of a carbon source, a growth medium containing oxygen and other essential cell nutrients, within which media the carbon source and each of the other essential cell nutrients are added, incrementally or continuously, to maintain the concentration of each respectively, at essentially the minimum level at which it is needed for most efficient assimilation, or utilization, by the cells in accordance with a predetermined growth rate curve, in its metabolic or respiratory function of converting the carbon source to a cell mass, or biomass. In conducting the process, each nutrient is added to the liquid fermentation media in accordance with the predetermined minimum requirements of the cell, or microorganism, in direct proportion to the biomass actually present in the media at the moment of addition. At the beginning of the fermentation, each nutrient is added in direct proportion to the amount of cells used for innoculation of the media. As fermentation proceeds, and the biomass grows, the concentration of each essential nutrient added to the fermentation media is increased in direct proportion to the rate of growth of the biomass. The net effect is that the concentration of each nutrient fed into the fermentation media is progressively increased throughout the period of fermentation. In such process, it is preferred to add the nutrients below the surface of the media, or below the level of the foam which invariably forms on the surface of the media. This assures rapid dispersion of the nutrients within the media, and a speedier and fuller utilization thereof by the cells.

In conducting any given fermentation pursuant to the practice of this invention, it is first necessary to predetermine the individual nutrient requirements for a given cell, or microorganism, at a desired set of operating conditions over the time period that the fermentation run is to be conducted, i.e., over an operating period beginning from initiation of a fermentation (time "zero") up to the time that the growth of the cell, or microorganism, has substantially ceased. This is accomplished by first establishing, or predetermining, suitably in a continuous culture media, the minimum requirements of a given cell, or microorganism, for a given nutrient. In such technique, the cells are starved of a particular nutrient while all other required nutrients are provided in quantity adequate to sustain growth of the culture and, when growth has ceased because of the need of the particular nutrient of which the cells have been deprived, the nutrient is then added in measured increments until cellular growth is resumed. Growth is resumed at that point in time when the minimum requirements of the cell, or microorganism, for the nutrient of which it had been deprived has been satisfied. The resumption of growth, produced by the addition of a measured amount of the required nutrient thus establishes the minimum requirements of the nutrient for the biomass actually present in the fermentation media at the time of addition. Such measurements, for each required nutrient, conducted over the entire period of fermentation, ranging from low biomass to high biomass concentrations, as from the beginning to the end of the fermentation period, establishes the minimum requirements for any given nutrient over the whole period of fermentation. The growth rate of a cell, or microorganism, in any culture medium is characteristically exponental, i.e., the rate of increase of a cell mass in proportional to the cell mass that is present at any given moment. In such system the cells are thus in a state of balanced growth or synthesis wherein every component of the growing system increases by the same factor or in proportion to the cells present at any given time, to wit: $dB/dt = aB$, where B is the cellular mass, $t$ is time and, $a$ is the instantaneous rate constant for the microorganism at the conditions. In accordance with the present invention, the growth rate of the cell mass is also exponential in character, although in accordance therewith the rate of growth of the cell mass is greatly increased, i.e., the instantaneous rate constant, $a$, is increased at any given set of conditions as contrasted with prior art fermentation processes.

Once the minimum known requirements of the cellular mass, or biomass, for each of the required nutrients has been established at any given point in time, from time zero to the end of the fermentation period, feed containing the minimum required amount of each nutrient for maximum growth can be incrementally or continuously added. This can be conveniently accomplished by feeding each nutrient as a feed of predetermined composition (i.e., fixed concentration of the nutrient in a liquid medium) into the fermentation media by use of a pump operated at a constant rate of flow, approximating the log function, or straight line function, of the established growth curve; or, by injection of such feed from a computer controlled pump the motor of which is actuated to vary the pump output and consequently the feed input in proportion to the preestablished minimum nutrient needs of the cells. By injection of each of the nutrients in direct proportion to the minimum need requirements of the cell, or microorganism, without significant excess thereof, considerably higher rates of cellular growth and consequently higher rates of production are achieved over a given period, and far greater amoounts of cells can be produced in the fermentation. In the best mode of practicing the present invention, each respective nutrient is supplied to the growing biomass in concentration ranging no greater than about 400 percent, and preferably no greater than about 10 percent in excess of the predetermined minimum amount of the respective nutrient, per 2.5 grams of cells per liter of the liquid media within which the cells are contained.

In one of its more preferred aspects, the present invention comprises a process for the preparation in a nutrient medium of comestible, digestible protein from a carbon source, suitably a hydrocarbon or carbohydrate, notably delignified cellulose. A cellulose elaborating microorganism, suitably a fungii, yeast or bacteria, notably a microorganism of the genus Cellulomonas (ATCC-21399) is used alone or in compatible association with another microorganism, and each of the required nutrients is added, incrementally or continuously, to the medium to maintain the concentration of each nutrient respectively, at essentially the minimum level at which it is needed for most efficient assimilation, or ultilization, by the microorganism in its metabolic or respiratory function of converting the carbon source to protein. In accordance therewith, aqueous medium is charged into the zone wherein the fermentation is to be conducted (i.e., fermentation zone), the medium is innoculated with the desired microorganism, or microorganisms, continuously stirred, the introduction of oxygen (air) is begun and the system then brought to the desired temperature and pH levels. Fermentation is initiated, and maintained, by incrementally or continuously adding each of the required nutrients to the fermentation medium in minimum amount assimilable by the microorganism in proportion to a predetermined growth rate of the microorganism, the growth rate being a metabolic or respiratory function or the respective microorganism, at extant conditions, in coverting the carbon source to protein.

In its most preferred aspects, a delignified cellulose substrate is employed as the carbon or energy source, the fermentation is conducted at submerged aerobic conditions in a stirred aqueous medium, the fermentation is conducted at temperatures ranging from about 25° C to about 40° C, and at pH ranging from about 5 to about 9, preferably from about 6 to 7. The medium is innoculated with a cellulose-elaborating microorganism, preferably of the genus Cellulomonas (ATCC-21399), and all of the nutrients are incrementally or continuously added, preferably below the foam, each amount based on the expected rate of microbial growth, as preestablished by determining the growth curve of the entire biomass where each of the nutrients are added in minimum required concentration.

In the formation of the carbon substrate for use in the fermentation zone, in the preferred embodiment, cellulose from any suitable source is first delignified, preferably by treatment with an alkali. Suitably, it is subjected to treatment by direct contact with an alkaline reagent or solution, preferably an aqueous solution of an alkali hydroxide, e.g., sodium hydroxide, in concentration sufficient to partially hydrolyze or solvate the cellulose. Preferably, the cellulose is treated with an aqueous alkali metal hydroxide solution, wherein the alkali metal hydroxide is present in concentration ranging from about 0.5 percent to about 75 percent, preferably from about 2 percent to about 50 percent, based on the weight of the total solution. Suitably, the physical size of the cellulose, if large, is reduced by cutting, sawing, grinding or crushing to assure intimate contact with the alkali. Suitably, the cellulose is simply immersed in a solution of the alkali. Most advantageously, the alkali hydroxides are hydroxides of Group I metals of the Periodic Table of the Elements, e.g., sodium, lithium, potassium, and the like, are employed, sodium hydroxide being especially preferred because of its cheapness, wide availability and effectiveness. Generally, the alkali treatment is conducted for periods ranging from about 0.1 hour to about 20 hours, or more, though time of treatment will vary in proportion to the kind, or nature, of the alkali used, its concentration or strength, the physical state, nature of the cellulose, its previous history of treatment, and upon the temperature of treatment. When using strong alkalis, e.g., alkali metal hydroxides such as sodium hydroxide, the alkali cellulose treatment is conducted at temperatures ranging from about $-10°$ C to about 70° C, preferably 10° C to about 30° C, from about 1 hour to about 24 hours. Advantageously, the time of treatment required to adequately hydrolyze the cellulose can be reduced by the addition of oxidation agents, of which Cobalt (II) chloride is illustrative. Highly efficient oxidation of the cellulose is achieved when the aqueous alkali contains from about 2 to about 500 parts by weight of an oxidation agent, e.g., Cobalt (II) Chloride, per million parts by weight of the alkali employed.

After contact between the cellulose and alkali, the treated cellulose is separated from the alkali by standard procedures known in the art, e.g., filtration, decantation, centrifugation, screening, passage between squeeze rolls, and the like. The alkali treated cellulose is then placed in an oxidation, or circulating air oven and heated, generally at temperatures ranging from about $-10°$ C to about 150° C, and preferably at temperatures ranging from about 25° C to about 100° C. The time period that the treated cellulose remains in the oven is not critical, periods generally ranging from about 0.1 hour to about 20 hours. Longer or shorter periods can be employed, the longer periods providing more complete digestion of the cellulose by the microorganisms in a subsequent step. Generally, an optimum balance is maintained based on process economics. Air is blown on the cellulose during this period to accelerate the rate of oxidation and hydrolysis of the cellulose.

The oxidized, alkali-treated cellulose is next removed from the oven, treated ex situ to a pH ranging between 5 and 9, e.g., a pH of 7, and then charged into a fermentor (or charged into the fermentor and then treated in situ to a pH ranging between 5 and 9), after which time, at the startup of fermentation, the cellulose is innoculated with the microorganism to be cultivated, and harvested. Adjustment of the pH is generally accomplished by addition of an aqueous acid solution, or proton donor, e.g., hydrochloric acid, with agitation sufficient to thoroughly contact the cellulose with the acid and establish equilibrium conditions. Within the fermentor, comprising a closed vessel, a draft tube and air lift are provided to maintain vigorous agitation and suitable aerobic conditions. The desired pH is maintained while providing optimum growth temperatures of the microorganisms to be harvested. If the pH becomes too high for optimum growth of the microorganisms to be harvested, it can be lowered by addition of a suitable acid to the fermentation media, or should the pH become too low, it can be raised by addition of a suitable base, e.g., ammonia or ammonium hydroxide.

The presence of oxygen is essential in the cultivation medium. Oxygen can be supplied to the cultivation medium in any form capable of being assimilated readily by the inoculant microorganisms, and oxygen-containing compounds can be used as long as they do not adversely affect microorganism cell growth and conversion of cellulose to microorganism cells. Conveniently, however, the oxygen is supplied as an oxygen-containing gas, e.g., air, which contains from 19 to 22 wt. percent oxygen. While it is preferably to employ air, oxygen enriched air having more than 22 wt. percent oxygen, e.g., enriched air having in excess of 22 wt. percent oxygen, can be used.

The presence of nitrogen is also essential to biosynthesis. Nitrogen is a required nutrient, and its source can be any organic or inorganic nitrogen-containing compound which is capable of releasing nitrogen in a form suitable for metabolic utilization by the harvested microorganism. In the organic category, the following compounds are listed as exemplary nitrogen-containing compounds which can be used: proteins, acid-hydrolyzed proteins, enzyme-digested proteins, amino acids, yeast extract, asparagine, urea, and the like. For reasons of economy, it is usually preferably to employ inorganic nitrogen compounds, such as: ammonia, ammonium hydroxide, or salts thereof, such as ammonium citrate, ammonium sulfate, ammonium phosphate, ammonium acid phosphate, and the like. A convenient and satisfactory method of supplying nitrogen is to employ ammonium phosphate or ammonium acid phosphate, which can be added as the salt, per se, or can be produced in situ in the aqueous fermentation media by bubbling nascent nitrogen through the broth to which phosphoric acid was previously added, thereby forming ammonium acid phosphate.

In addition to the energy and nitrogen sources, it is necessary to supply requisite amounts of selected mineral nutrients in the feed medium in order to insure proper microorganism growth and maximize selectivity, e.g. in the conversion of cellulose to microorganism cells. Thus, potassium, sodium, iron, magnesium, calcium, manganese, phosphor, and other nutrients are included in the growth medium. These necessary materials can be supplied in the form of their salts, and preferably their water-soluble salts. For example, potassium can be supplied as potassium chloride, phosphate, sulfate, citrate, acetate, nitrate, etc. Iron and phosphorus can be supplied in the form of sulfates and phosphates, respectively, e.g., iron sulfate, iron phosphate. Usually, most of the phosphorus is supplied as ammonia phosphates. When either ammonium phosphates or ammonium acid phosphate is used, it can serve as a combined source of both nitrogen and phosphorus (phosphate ion) for microorganism cell growth.

In the practice of this invention, at the startup of fermentation, the liquid within which the fermentation is to be conducted, usually water, is charged to the fermentation vessel (fermentation zone) and it is innoculated with the cell culture, microorganism, or microorganisms, to be harvested, e.g., by use of a previously cultivated inoculum in the same media in which it is to be grown. The initial concentration of inoculum containing said microorganisms at the outset of fermentation can vary widely, e.g., 0.0005 to 50 grams per liter of total fermentation media. Other inoculation procedures can be employed, e.g., use of an inoculum where said microorganisms are previously grown on a media different from that in which the fermentation is to be conducted and then transferred to the fermentation vessel. The contents of the vessel are continuously agitated, the fermentation media is brought to the desired temperature and pH level, and air (oxygen) is continuously introduced to provide a predetermined oxygen level. The carbon, nitrogen and phosphorus sources, and trace mineral elements, all of which are essential cell nutrients are each then added, incrementally or continuously, to the fermentation media at essentially the minimum level needed for the most rapid assimilation by the growing cells in accordance with a predetermined cell growth rate curve, in the metabolic function of the cells in converting the carbon source to a biomass. In such additions care is taken to avoid admixing of any of the several ingredients under conditions which would produce precipitation. The minimum requirements of these required nutrients established for a Procaryotes, a non-spore former, Cellulomonas (ATCC-21399) and a spore former, Bacillus Cereus, and a Eucaryotes, or yeast Candida, at the conditions identified in the following tabulation.

| | Concentration, grams per liter per 2.5 grams of biomass per liter of solution | | |
|---|---|---|---|
| Component | Cellulomonas[1] | Bacillus[2] Cereus | Candida[3] |
| $(NH_4)_2SO_4$ | 0.975 | " | " |
| $K_2HPO_4$ | 0.234 | " | " |
| $NaH_2PO_4 \cdot H_2O$ | 0.078 | " | " |
| Glucose | 5 | " | " |

| | Concentration, grams per liter per 2.5 grams of biomass per liter of solution | | |
|---|---|---|---|
| Component | Cellulomonas[1] | Bacillus[2] Cereus | Candida[3] |
| Thiamine | 0.005 | yeast extract added | yeast extract added |
| Pantothenate | 0.005 | | |
| Biotin | 0.0002 | | |
| $ZnSO_4 \cdot 7H_2O$ | 0.0008 | " | " |
| $CoCl_2 \cdot 6H_2O$ | 0.00002 | " | " |
| $CuSO_4 \cdot 5H_2O$ | 0.0000005 | " | " |
| $MnCl_2 \cdot 4H_2O$ | 0.00001 | " | " |
| $MgCl_2 \cdot 6H_2O$ | 0.1 | " | " |
| $CaCl_2 \cdot 2H_2O$ | 0.01 | " | " |
| $FeSO_4 \cdot 7H_2O$ | 0.0025 | " | " |

[1]Fermentation conducted at pH of 6.8, temperature of 35° C, and air introduced at rate of 1-2 volumes per volume of liquid media per minute.
[2]Fermentation conducted at pH of 6.5, at temperature of 30° C, and air is introduced at rate of 1-2 volumes per volume of liquid media per minute.
[3]Fermentation conducted at pH of 5.0, at temperature of 30° C, and air is introduced at rate of 1-2 volumes per volume of liquid media per minute.

In these systems it is found that suitable cellular growth can be sustained if the additions are made in concentrations ranging about four times the minimum requirement, but preferably the concentrations of nutrient should be maintained within about 10 percent of the predetermined minimum concentration.

Various other carbon, nitrogen, phosphorous, and trace mineral sources can, of course, be employed. Optional nutrients and vitamins can also be added to a particular fermentation system, preferably also by incremental or continuous addition based on the minimum requirements of the cell, or microorganism, if desired; although, there is no necessity to add non-required nutrients or vitamins in this manner. At the end of fermentation, the cells, or microorganisms, are isolated from the fermentation media by decantation, filtration, centrifugation, and the like. The filtered cells can then be dewatered, using e.g., rotary drum dryers, spray dryers, and the like. For some purposes it is unnecessary to render the cells non-viable. Where this is desired, however, the cells are usually rendered non-viable before use by spray drying at 150°-185° C for from about 2 to about 30 seconds. Care should be exercised during pasteurization to avoid extreme temperatures for extended time periods when the harvested cells are to be used as protein supplement, or protein degradation can result.

The following non-limiting examples are illustrative, and bring out more salient features of the invention. All parts and percentages are given in terms of weight, weight units being expressed in grams.

EXAMPLE 1

Growth of Cellulomonas in gradient feed culture

Cellulomonas (ATCC-21399) was fermented in a continuously stirred aqueous medium contained in a New Brunswick 7 liter fermentation vessel at 35° C, at a pH of 6.8, air being introduced at a rate of 1-2 volumes of air per volume of aqueous medium per minute. In initiating the fermentation reaction, 4.5 liters of the medium containing the following ingredients was inoculated with 500 ml of an overnight culture of said Cellulomonas, to wit:

| | g/l |
|---|---|
| Glucose | 5 |
| $(NH_4)_2SO_4$ | 0.75 |
| $K_2HPO_4$ | 0.18 |
| $NaH_2PO_4 \cdot H_2O$ | 0.06 |
| $MgCl_2 \cdot 6H_2O$ | 0.1 |

-continued

|  | g/l |
|---|---|
| $CaCl_2 \cdot 2H_2O$ | 0.01 |
| $FeSO_4 \cdot 7H_2O$ | $2.5 \times 10^{-3}$ |
| $ZnSO_4 \cdot 7H_2O$ | $2 \times 10^{-3\,[14]}$ |
| $CoCl_2 \cdot 6H_2O$ | $2 \times 10^{-5}$ |
| $CuSO_4 \cdot 5H_2O$ | $5 \times 10^{-7}$ |
| $MnCl_2 \cdot 4H_2O$ | $1 \times 10^{-5}$ |
| Biotin | $2 \times 10^{-4}$ |
| Thiamin | $5 \times 10^{-3}$ |

The organism was allowed to grow until the growth as measured by absorbance showed 500–700 Klett units (approximately 1.5 to 2.0 g/liter of cells), which time is considered as the start of the experiment, time zero ($t_o$). Concentrated nutrients were pumped into the fermenter in such manner the nutrient concentrations increased as a linear gradient with time to the end of the run ($t_{10}$), the final concentration of nutrients coming into the fermenter being equivalent to 10 × the initial concentration of the nutrients. The total time of pumping was 10 hr. The total volume of additional nutrients was kept between 500–800 ml, thus allowing for the loss in evaporation during aeration of the fermenter contants. The increase in volume of the culture was about 10% of the original volume. Growth was monitored at intervals by taking samples of the culture and measuring the turbidity with a Klett-Summerson colorimeter. Results of a typical experiment are presented in Table 1, as follows:

Table 1

| Time (Hr) | Absorbance (Klett units) | Dry wt, g/l. |
|---|---|---|
| $t_0$ | 700 | 2.1 |
| $t_2$ | 1850 | 5.5 |
| $t_3$ | 2600 | 7.8 |
| $t_5$ | 4200 | 12.6 |
| $t_{10}$ | 9800 | 29.4 |

In sharp contrast in a run conducted at similar conditions except that all of the nutrients were added ab initio to the fermentation vessel, at the end of a 36 hour period, the biomass was only 15.0 Dry Wt, g/l.

EXAMPLE II

Growth of Bacillus cereus in gradient feed culture

The procedure of cultivation of Bacillus cereus for this Example II is similar to that of Cellulomonas but with the following modifications:

The medium composition used in this experiment was similar to that of Cellulomonas except that the vitamins were replaced by yeast extract (0.1 g/liter).

The final concentration of glucose in the gradient was 2% and the other nutrients were proportionately adjusted.

The inoculum was allowed to grow to an absorbance of 27 Klett units when the experiment was started and the total time of the experiment was six hours as compared to 10 hrs for Cellulomonas.

Initial and final yield of cells are presented in Table II.

EXAMPLE III

Growth of Yeast by the gradient feed method

Candida guillermondii (GSU-1) was used in these studies.

The initial medium for the experiment was similar to that in Bacillus cereus. However the pH was adjusted to 5.0 before the experiment was started, and the final concentration of glucose in the gradient was 5% and the other nutrients were proportionately adjusted.

The total time of the experiment was 12 hrs. The results are also presented in Table II, which also summarizes the results of all of the experiments described in Examples I, II and III, as relates to the practice of this invention.

Table II

| Organism | Experimentation | Absorbance in K.U. start | Absorbance in K.U. final | Increase | generations | Ave. doubling time |
|---|---|---|---|---|---|---|
| Cellulomonas sp. | 10 hr | 700 | 9800 | 14 × | 3.80 | 2.63 |
| Bacillus cereus | 6 hr | 27 | 1500 | 55 × | 5.78 | 1.03 |
| Candida guillermondii | 12 hr | 440 | 5200 | 11.8 × | 2.40 | 5.00 |

EXAMPLE IV

Growth of Cellulomonas in gradient feed culture with other carbon substrates

Further tests were conducted at the conditions described in Example I with Cellulomonas, pursuant to this invention, using carbon sources other than glucose in the fermentation vessel, to wit: alkali treated Solka floc and bagasse. The results of these tests are given in the following Table III:

Table III

| Carbon Source | Volume of Fermentation | Time of Fermentation | Biomass Dry Wt., g/l |
|---|---|---|---|
| Solka floc | 5 liters | 24 hours | 18–20 |
| Bagasse | 5 liters | 36 hours | 18.0 |

It is apparent that various changes, such as the precise identity of the carbon source, the nature of the salts added to provide such essential nutrients as nitrogen and phosphorous, or in temperature and pH ranges, can be made without departing the spirit and scope of the invention, as will now be apparent to those skilled in the fermentation art. The fermentation systems described, though preferred, are offered as illustrations and numerous applications of the present inventive process to various fermentation systems will readily be apparent to those skilled in this art.

Carbon sources for cell growth are hydrocarbons, e.g. $C_1$ to $C_{30}$ hydrocarbons, i.e., $C_1$ to $C_5$ gaseous paraffins, $C_6$ to $C_{10}$ naphthas, $C_{11}$ to $C_{30}$ gas oils and the like. Suitably, where the hydrocarbons are to be converted to food, the feeds should contain a minimum of aromatics. Suitable microorganisms for converting hydrocarbons to protein are, e.g. Pseudomonas, Nocardia and Mycobacterium.

Cellulose is a preferred carbon source. Chemical celluloses, e.g., nitrocellulose, ethyl cellulose, cellulose acetate, methyl cellulose, carboxymethyl cellulose, and regenerated cellulose products, e.g., viscose, rayon, cuprammonium rayon, cellophane, sausage casings, and the like, and delignified cellulose from any source may be used as an energy or carbon substrate in accordance with this invention.

Waste cellulosic materials, in particular, can be readily converted into nutritive protein. Illustrative of such cellulosic wastes are cotton linters, bagasse, rice straw, sawdust, Johnson grass, prairie grass, alfalfa meal, cottonseed hulls, corn cobs, oat straw, and sorghum bagasse. Other waste cellulose which may be advantageously employed with proper treatment are industrial cellulosics such as packaging materials and wastes from wood and pulp industry, agricultural wastes such as bagasse, and general urban wastes such as paper bags, newspapers, books, magazines, and the like.

It is necessary to supply sufficient mineral nutrients to insure proper microorganism growth and maximize selectivity, viz., the growth of cells. Thus, potassium, sodium, iron, magnesium, calcium, manganese, phosphorous, and other nutrients are included in the aqueous growth medium. These necessary materials can be supplied from various sources, but usually are supplied as additives in the form of their salts, preferably water-soluble salts.

The key and novel feature of the present invention, however, resides primarily in the mode of addition of the essential nutrients, viz: each is supplied at essentially the minimum level needed for the most efficient assimilation by the cells to maximize, at a given cell density, the growth rate of the cell, or organism, and the minimum level for each nutrient can be readily pre-established to achieve this end.

Having described the invention what is claimed is:

1. In a process for biosynthetically cultivating cells in an aqueous fermentation medium comprising a carbon source, nitrogen, phosphorus, trace mineral elements, and oxygen in amount sufficient to provide a predetermined oxygen level, to obtain a biomass of such cells for harvesting, the improvement which comprises adding the carbon source, nitrogen, phosphorus, and each of the trace mineral elements to the fermentation medium, incrementally or continuously, and maintaining each throughout fermentation at essentially the minimum level required for assimilation by the cells to sustain growth, thereby maximizing the cellular growth rate; said minimum requirements for the carbon source, the nitrogen, the phosphorus and each of the trace mineral elements having been established in accordance with a predetermined cell growth rate curve, said predetermined cell growth rate curve having been independently established for the carbon source, the nitrogen, the phorphorus, and each of the trace metal elements, at different biomass levels in a continuous culture medium as occurs from the beginning of fermentation to the end of the period of growth of the cells in the fermentation medium, by starving the growing cellular mass of a nutrient, the minimum concentration of which is to be established while all other of the required nutrients are provided in quantity adequate to sustain growth of the cellular mass and, when growth has ceased due to a lack of the particular nutrient of which the cells have been deprived, adding the nutrient in measured incremental concentrations until growth of the cells has resumed.

2. The process of claim 1 wherein each of the essential nutrients is added to the fermentation medium in concentration ranging no greater than about 10 percent in excess of the predetermined minimum amount of said minimum cell requirements, per 2.5 grams of cells per liter of fermentation media.

3. The process of claim 1 wherein the cells are comprised of a microorganism selected from the group consisting of Cellulomonas, Bacillus cereus, and Candida.

4. The process of claim 1 wherein the cells are comprised of a microorganism of the genus Cellulomonas cultivated as a source of single cell protein, the carbon source is an alkali treated cellulose, and the cultivation of the microorganism is conducted under submerged aerobic conditions at a temperature ranging from about 25° C to about 40° C at pH ranging from about 5 to 9.

5. The process of claim 1 wherein the pH ranges from about 6 to 7.

6. The process of claim 1 wherein, during the cultivation, the carbon source and all nutrients are added to the fermentation medium below a foam which forms on top of the fermentation medium.

* * * * *